United States Patent [19]

Graham

[11] 4,221,779
[45] Sep. 9, 1980

[54] PHARMACEUTICAL COMPOSITION FOR TREATING TROPICAL DISEASES

[76] Inventor: Neil B. Graham, 6 Kilmardinny Grove, Bearsden, Dunbartonshire, England

[21] Appl. No.: 920,056

[22] Filed: Jun. 28, 1978

[30] Foreign Application Priority Data

Jun. 28, 1977 [GB] United Kingdom ............... 26918/77

[51] Int. Cl.² ...................... A61K 31/74; A61K 47/00
[52] U.S. Cl. ...................................... 424/78; 424/365; 528/271
[58] Field of Search .................. 424/78, 365; 528/271

[56] References Cited

U.S. PATENT DOCUMENTS

| | | | |
|---|---|---|---|
| 3,316,325 | 4/1967 | Allan | 526/333 |
| 3,318,846 | 5/1967 | Smith et al. | 526/330 |

OTHER PUBLICATIONS

Chem. Abst. 66 116282(k), (1967), Canadian Industrials Ltd.

Chem. Abst. 76 100462(q), (1972), PaPa.

*Primary Examiner*—Douglas W. Robinson
*Attorney, Agent, or Firm*—Finnegan, Henderson, Farabow, Garrett & Dunner

[57] ABSTRACT

A pharmaceutical composition of prolonged effect in the treating of Tropical Diseases comprises an organic nitrogen base drug which is effective against diseases such as malaria, dispersed in a polymeric matrix of a copolymer of the compound

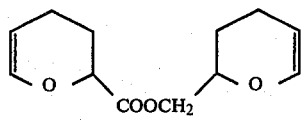

and a comonomer which contains more than one functional group selected from hydroxy and carboxy groups.

10 Claims, No Drawings

PHARMACEUTICAL COMPOSITION FOR TREATING TROPICAL DISEASES

The present invention relates to pharmaceutical compositions for the treatment of tropical disease.

Tropical diseases, for example malaria and leprosy, have hitherto been prevented and treated by periodic administration of a dose of a drug to combat offending parasites present in the body. The drug is generally administered orally or by injection, and passes through the body so that frequent dosage is necessary.

An object of this invention is to provide a composition which is effective against tropical disease and which can provide a prolonged supply of a drug to a body with infrequent administration.

According to the present invention there is provided a composition for use in the treatment of tropical disease, comprising a drug which is an organic compound containing a nitrogen atom and which is effective against tropical disease in admixture with a polymeric matrix of a copolymer of the compound of the formula

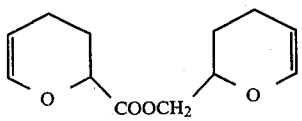

(I)

with at least one compound having more than one functional group selected from OH and COOH groups.

Drugs of particular effectiveness are, cycloguanil, pyrimethamine and sulphadiazine.

Drugs which are effective against tropical disease normally contain nitrogen atoms and are consequently basic in character. This can cause considerable problems in the preparation of the composition of this invention as the copolymerisation reaction between the compound of formula I and the compound or compounds having more than one OH or COOH group is acid catalysed; thus, admixture of such a drug with the copolymerisation reactants can result in a neutralisation reaction between the drug and the acid catalyst with consequent prevention or restriction of the copolymerisation.

Strongly basic drugs, if soluble in the copolymerisation reaction medium, therefore inhibit the copolymer formation, and this can be overcome either (a) by selecting an insoluble drug or rendering the drug insoluble and forming a dispersion rather than a solution, or (b) by using the drug in the form of its salt, preferably fully neutralised.

The use of soluble bases requires very large amounts of acid catalyst for the copolymerisation.

Examples of tropical disease which can be prevented or treated by compositions of this invention are malaria, leprosy, schistosomiasis and clonorchiasis.

Examples of drugs which can be used in the present composition to combat these and other tropical diseases are quinine, sulphonamides, chlorphenyl derivatives, chloroguanide, pyrimethamine, trimethoprim, quinoline derivatives such as pamaquine, chloroquine, pentaquine, primaquine and amodiaquine, pararosaniline, sulphamethizole, quinacrine, dapsone, sodium sulphoxone, sulphetrone, sodium hydnocarpate and sodium chaulmoograte.

The compound having two or more groups selected from OH and COOH groups is preferably a compound which occurs naturally in and/or is benign to the human body. Examples of compounds containing two or more groups selected from OH and COOH groups which can be used in the present invention are:

(a) among the compounds having two or more OH groups, glycerol, sorbitol, erythritol, inositol, glycols based on polyethylene oxide, 4,4'-dihydroxyphenyl-2,2-propane, 1,2-dihydroxy-benzene, 1,3-dihydroxy-benzene, 1,4-dihydroxy-benzene, 1,2,3-trihydroxy-benzene, 1,2,4-trihydroxy-benzene, 1,3,5-trihydroxy-benzene and the like;

(b) among the compounds having at least one OH group and at least one COOH group, lactic acid, malic acid, 2-hydroxy-isobutyric acid, 10-hydroxydecanoic acid, 12-hydroxyoctadecanoic acid, 12-hydroxy-(cis)-9-octadecenoic acid, 2-hydroxycyclo-hexanecarboxylic acid (hexahydrosalicyclic acid), 2-hydroxy-2-phenyl-(D)-propionic acid, diphenylhydroxyacetic acid, ascorbic acid, citric acid, tartaric acid, 2 hydroxy-3-methyl-(D) succinic acid, 2-hydroxybenzoic acid, 3-hydroxybenzoic acid, 4-hydroxybenzoic acid, 2,3-dihydroxybenzoic acid, 2,4-dihydroxybenzoic acid, 2,5-dihydroxybenzoic acid, 2,6-dihydroxybenzoic acid, 2,3,4-trihydroxybenzoic acid, 2,4,5-trihydroxybenzoic acid, 2,4,6-trihydroxybenzoic acid, 3,4,5-trihydroxybenzoic acid and the like;

(c) among the compounds having two or more COOH groups, oxalic acid, malonic acid, succinic acid, glutaric acid, adipic acid, 1,2-cyclohexanedicarboxylic acid, 1,3-cyclohexane-dicarboxylic acid, 1,4-cyclohexanedicarboxylic acid, phthalic acid, isophthalic acid, teraphthalic acid and the like.

The ratio of drug to copolymer which can be present in the compositions of this invention can vary within wide limits. Preferably the weight of the drug is at least about equal to the weight of copolymer, and it may be possible to have a steroid to copolymer weight ratio of up to 90:10. A steroid to copolymer ratio of form about 50:50 by weight to about 60:40 by weight is particularly suitable.

According to the process provided by the present invention, the compositions of this invention are prepared by copolymerising a compound of formula I hereinbefore with at least one compound having more than one group selected from OH and COOH groups in the presence of an acidic catalyst and in the presence of a drug effective against tropical disease.

The compound of formula I hereinbefore, which is a mixture of stereoisomers, is a colourless liquid having a high boiling point, a very low level of oral toxicity and no known detrimental effect on skin. It may be prepared according to the following reaction sequence:

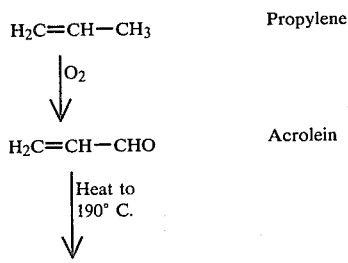

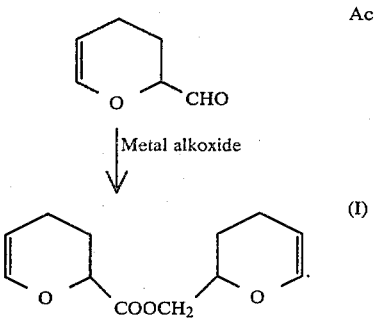

Acrolein dimer

Metal alkoxide (I)

The process provided by the present invention may be carried out by simply mixing the compound of formula I with a compound having two or more groups selected from OH and COOH groups or with a mixture of such compounds in the presence of an acidic catalyst, advantageously at an elevated temperature such as from about 60° C. to 100° C., especially at about 80° C., and then adding to the resulting mixture and homogeneously distributing therein the appropriate amount of the desired drug. The mixture thus obtained can then be allowed to cure, suitably at an elevated temperature.

It is preferable that the drug should not react with the catalyst, and it may therefore be in the form of a salt, for example its hydrochloride, or be insoluble in the reaction medium.

In certain circumstances it may be desirable to interrupt the copolymerisation during the initial mixing of the compound of formula I with a compound having two or more groups selected from OH and COOH groups or with a mixture of such compounds. This can be effected, for example, by the addition of an amount of a primary, secondary or tertiary amine such as triethylamine, a quaternary ammonium hydroxide or a basic inorganic oxide or hydroxide sufficient to neutralise the activity of the acidic catalyst. The drug preferably in salt form or in dispersion, can then be added to and homogeneously distributed in the resulting mixture and subsequently the copolymerisation can be allowed to proceed to completion by the addition of further acidic catalyst.

Suitable acidic catalysts which may be used in the present process include inorganic acids such as hydrochloric acid, sulphuric acid etc, organic acids such a paratoluenesulphonic acid etc and Lewis acids such as zinc chloride, tin tetrachloride, aluminum chloride, ferric chloride etc. The preferred acidic catalyst is ferric chloride. The amount of acidic catalyst used is not critical, but it is expedient to use from about 0.01% to 2.0%, particularly from about 0.04% to about 1.0% based on the total weight of the mixture.

The ratio of the compound of formula I to the compound having two or more groups selected from OH and COOH groups can be varied. It is convenient to use stoichiometric amounts, although the use of amounts which deviate considerably from stoichiometry is also possible.

The copolymerisation may also be carried out in the presence of an inert pharmaceutically acceptable solvent or an inert pharmaceutically acceptable oil, whereby the nature of the resulting medicinal composition is modified. An example of such an oil is olive oil. The inert pharmaceutically acceptable solvent or oil may be added as such or it may serve as a solvent or dispersant for other components of the copolymerisation mixture. Thus, for example, the drug may be dissolved or dispersed in the inert pharmaceutically acceptable solvent or oil.

The following is a simplified representation of the preparation of a cross-linked copolymer using the compound of formula I and glycerol:

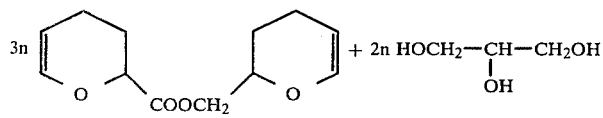

acidic catalyst

-continued

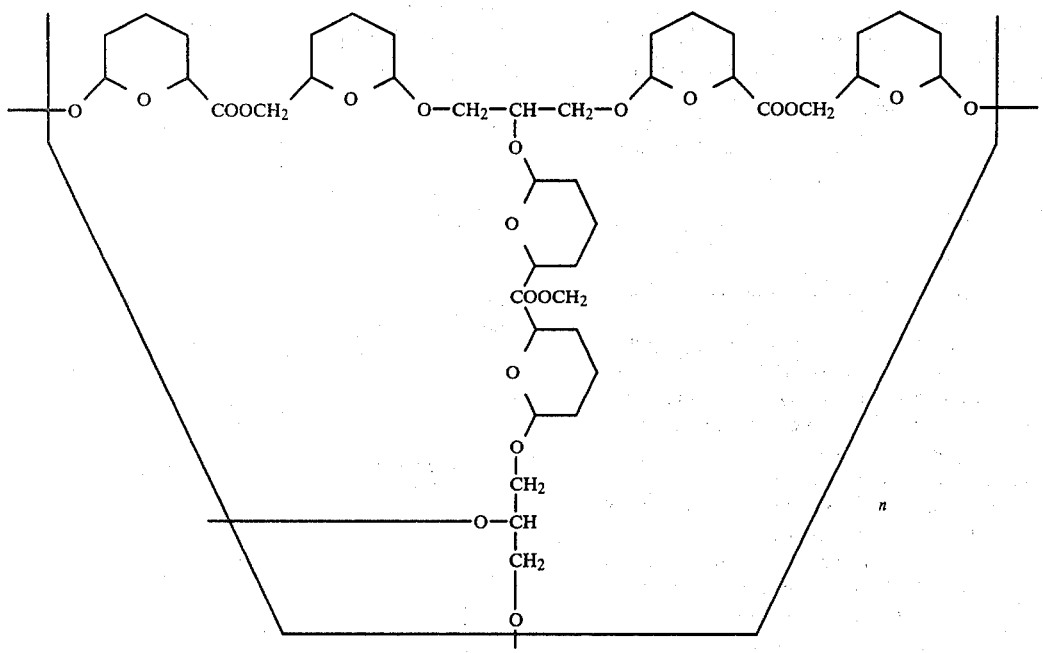

Following administration of the compositions of this invention to the body, the drug is gradually released therefrom over a prolonged period and, at the same time, the copolymer is biodegraded to substances which can be readily disposed of by the body. As mentioned earlier, the copolymer is preferably one formed between the compound of formula I and a compound which occurs naturally in and/or is benign to the human body. Hydrolysis, especially acid hydrolysis, of such copolymers yields predominantly the latter compounds themselves. In the case of a copolymer prepared using glycerol as illustrated hereinbefore, the hydrolysis fragments of the compound of formula I are the following:

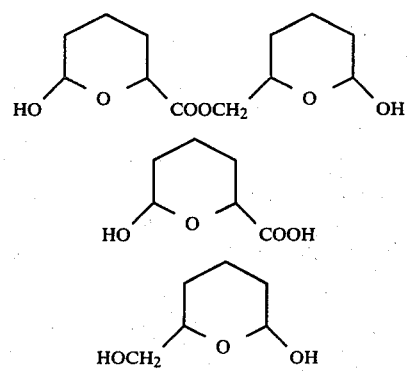

all of which are readily oxidisable for disposal by the body.

The rate of release of the drug from a composition provided by this invention can be controlled by a variety of methods.

For example, in a copolymer prepared using given components the density of the cross-linking can be altered. Again, for example, the nature and amount of inert pharmaceutically acceptable solvent or oil which may be present in the composition can be varied.

A particular feature of compositions provided by the present invention which are based on cross-linked copolymers (i.e. matrices) is that such copolymers have a so-called glassy state (in which they are hard and brittle) and a rubber-like state, the change from the glassy state to the rubber-like state occurring at the so-called glass transition temperature. Following administration of such a composition having the copolymer in the glassy state the drug is gradually released and, at the same time, the copolymer is gradually biodegraded, this resulting in a gradual reduction of the glass transition temperature. When the glass transition temperature is reached the rubber-like state occurs and the copolymer becomes more rapidly biodegraded. Thus, if the glass transition temperature reaches body temperature, there is a rapid onset in the degradation. It will accordingly be evident that it is highly desirable to provide compositions based on cross-linked copolymers which initially have a glass transition temperature which lies somewhat above body temperature.

The compositions provided by the present invention may be administered for example by subcutaneous or intramuscular injection or implantation. In the case of forms for injection a composition of appropriate particle size can be dispersed in a pharmaceutically acceptable carrier material adapted for subcutaneous or intramuscular administration. By appropriate choice of particle size and particle size distribution in the dispersant the rate of release of the drug can be controlled. Forms adapted for implantation include, for example, pellets, films, discs, rods and the like. Such implant forms can be prepared in a conventional manner.

In many cases it is of advantage to include in the composition of the invention a combination of drugs to obtain most effective prophylaxis or treatment of a tropical disease.

The following Examples describe embodiments of the present invention.

EXAMPLE 1

The following ingredients were used to prepare a polymer matrix having a ratio of compound I to glycerol of 3:2 and containing 50% by weight of norethisterone:

| | | |
|---|---:|---|
| Glycerol | 215.5 | mg |
| 3,4-Dihydro-2H-pyran-2-methyl-(3,4-dihydro-2H-pyran-2-carboxylate) (Compound I) | 790.0 | mg |
| Ferric chloride | 10.0 | mg |
| Amodiaquine | 53.4 | mg |

A solution of the ferric chloride in the glycerol is warmed to 80° C. and the compound I is added dropwise while warming and stirring between the additions. Compound I is initially incompatible with the glycerol, but by gradual additions and warming until the mixture becomes one phase, a stage is reached when the glycerol mixture will more readily accept the additions of compound I and become homogeneous.

After stoichiometric amounts of compound I to glycerol have been reached, the mixture is removed from the heating source and the amodiaquine is added to form a dispersion in the monomer mixture. A temperature of 80° C. is maintained until polymerisation is complete and the desired polymer matrix is obtained containing 5% of amodiaquine by weight.

The dispersion referred to in the preceding paragraph can be used to prepare discs for implantation as follows:

Prior to the final polymerisation stage, the dispersion is spread on a film of Polythene, covered with a second film of Polythene and placed in a press which, when closed, leaves a gap between the Polythene films of the desired thickness of the copolymer matrix. A temperature of 80° C. is applied until polymerisation is complete. The film of amodiaquine/polymer matrix is punched while still soft to produce flat discs and, after hardening has taken place, the Polythene backing is peeled off.

EXAMPLE 2

According to the procedure described in Example 1, the following ingredients were used to prepare a polymer matrix containing amodiaquine.

| | | |
|---|---:|---|
| Glycerol | 91.2 | mg |
| Compound I | 332.9 | mg |
| Ferric chloride | 42.4 | mg |
| Amodiaquine | 93.3 | mg |

This produced a composition containing 20% by weight of amodiaquine dispersed in the polymer matrix.

EXAMPLE 3

According to the method of Example 1, the following ingredients were used to prepare a composition comprising a dispersion of 25.8% of sulphamethizole in a polymer matrix.

| | | |
|---|---:|---|
| Glycerol | 215.5 | mg |
| Compound I | 790.0 | mg |
| Ferric chloride | 10.0 | mg |
| Sulphamethizole | 262.0 | mg |

EXAMPLE 4

According to the method of Example 1, the following ingredients were used to prepare a polymer matrix containing cycloguanil

| | | |
|---|---:|---|
| Glycerol | 238 | mg |
| Compound I | 1,035.9 | mg |
| Ferric chloride | 28 | mg |
| Cycloquanil | 147 | mg |

The composition was worked-up as pellets for subcutaneous implantation 6mm in diameter and 2mm thick.

In tests on mice prolonged effectiveness against *Plasmodium Bergei* has been observed over periods in excess of three months.

EXAMPLE 5

According to the method of Example 1, the following ingredients were used to prepare a polymer matrix containing sulphadiazine (SDA)

| | 10% SDA | 30% SDA |
|---|---:|---:|
| Glycerol | 3054 | 4277 mg |
| Compound I | 1115.6 | 1561.1 mg |
| Ferric chloride | 3.1 mg | 4.3 mg |
| Sulphadiazine | 165.2 mg | 854 mg |

The composition was worked-up as a powder and as an implant of the same dimensions as in Example 4.

The powdered product was tested in powder form of particle size (a) <53μ and (b) 53–96μ. The powder (a) was suspended in glycerol and injected into the test mice: powder (b) was implanted. Prolonged protection in excess of five months of the test mice against the action of *Plasmodium Bergei* has been observed.

EXAMPLE 6

According to the method of Example 1, the following ingredients were used to prepare a polymer matrix containing pyrimethamine.

| | | |
|---|---:|---|
| Glycerol | 3587 | mg |
| Compound I | 1314.1 | mg |
| Ferric chloride | 72 | mg |
| Pyrimethamine | 716.9 | mg |

The product was formed into a pellet for subcutaneous implantation into test mice. The mice were protected against *Plasmodium Bergei* for periods in excess of three months.

We claim:

1. A pharmaceutical composition comprising therapeutically effective amount of a drug which is an organic compound containing a nitrogen atom and which is effective against a tropical disease, in admixture with a polymeric matrix of a copolymer of the compound of Formula I:

(I)

with at least one comonomer having more than one functional group selected from the group consisting of hydroxyl and carboxyl groups, said polymeric matrix being biodegradable in the body.

2. A pharmaceutical composition according to claim 1, in which the polymeric matrix is a copolymer of glycerol and the compound of Formula I defined in claim 1.

3. A pharmaceutical composition according to claim 2, in which the molar ratio of the compound of formula I to glycerol is 3:2.

4. A pharmaceutical composition comprising 10%(wt.) cycloguanil dispersed in a polymeric matrix of a copolymer formed from a mixture containing 17%(wt.) glycerol, 73.8%(wt.) of the compound having the following structural formula:

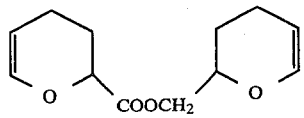

and 0.2%(wt.) ferric chloride.

5. A pharmaceutical composition comprising 10%(wt.) sulphadiazine dispersed in a polymeric matrix of a copolymer formed from a mixture containing 20%(wt.) glycerol, 69.8%(wt.) of the compound having the following structural formula:

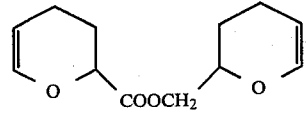

and 0.2%(wt.) ferric chloride.

6. A pharmaceutical composition comprising 30%(wt.) sulphadiazine dispersed in a polymeric matrix of a copolymer formed from a mixture containing 15%(wt.) glycerol, 54.8%(wt.) of the compound having the following structural formula:

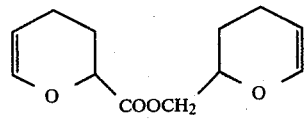

and 0.2%(wt.) ferric chloride.

7. A pharmaceutical composition comprising 30%(wt.) pyrimethamine dispersed in a polymeric matrix of a copolymer formed from a mixture containing 15%(wt.) glycerol, 54.7%(wt.) of the compound having the following structural formula:

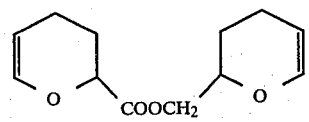

and 0.3%(wt.) ferric chloride.

8. A pharmaceutical composition comprising a therapeutically effective amount of a drug which is an organic compound containing a nitrogen atom and which is effective against a tropical disease in admixture with a polymeric matrix having a glass transition temperature above body temperature which is prepared by mixing the compound of Formula I:

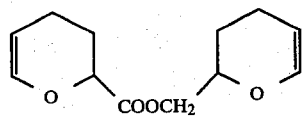

(I)

with glycerol in the presence of an acidic catalyst, adding said drug to the resulting mixture and then permitting said mixture to cure.

9. A pharmaceutical composition according to claim 8 wherein the compound of formula I and glycerol are admixed in a molar ratio of 3:2.

10. A pharmaceutical composition according to claim 9 wherein the acidic catalyst is ferric chloride.

* * * * *